United States Patent [19]

Bondi et al.

[11] Patent Number: 4,730,013

[45] Date of Patent: Mar. 8, 1988

[54] BIOSOLUBLE OCULAR INSERT

[75] Inventors: Joseph V. Bondi, Collegeville; Richard J. Harwood, Bensalem, both of Pa.

[73] Assignee: Merck & Co., Inc., Rahway, N.J.

[21] Appl. No.: 20,616

[22] Filed: Mar. 2, 1987

Related U.S. Application Data

[63] Continuation-in-part of Ser. No. 679,411, Dec. 7, 1984, abandoned, which is a continuation-in-part of Ser. No. 491,114, May 3, 1983, abandoned, which is a continuation-in-part of Ser. No. 309,852, Oct. 8, 1981, abandoned.

[51] Int. Cl.$^4$ .............................. A61K 9/22; C08L 1/26
[52] U.S. Cl. ......................................... 524/42; 524/58; 523/105; 424/427; 424/428
[58] Field of Search ............................. 524/43, 42, 58; 523/105, 108; 604/893, 894

[56] References Cited

U.S. PATENT DOCUMENTS

| | | |
|---|---|---|
| 3,968,201 | 7/1976 | Ryde et al. ........................... 128/261 |
| 3,993,071 | 11/1976 | Higuchi et al. ..................... 128/130 |
| 4,179,497 | 12/1979 | Cohen et al. ....................... 128/260 |
| 4,343,787 | 8/1982 | Katz ................................... 604/894 |

FOREIGN PATENT DOCUMENTS

| | | |
|---|---|---|
| 00108765 | 5/1980 | European Pat. Off. . |
| 1360927 | 7/1974 | United Kingdom . |
| 1359198 | 7/1974 | United Kingdom . |

*Primary Examiner*—Delbert R. Phillips
*Assistant Examiner*—Nathan M. Nutter
*Attorney, Agent, or Firm*—William H. Nicholson; Michael C. Sudol

[57] ABSTRACT

Ocular inserts with or without pharmacologically active agents comprising low molecular weight polymers have a lower propensity to cause blurred vision compared with inserts prepared from high molecular weight hydroxypropyl cellulose. When an enteric coating material is included as a constituent of the matrix there is provided a means for controlling and predicting dissolution rates of the insert to yield a prolonged residence time.

2 Claims, No Drawings

BIOSOLUBLE OCULAR INSERT

This is a continuation-in-part of application Ser. No. 679,411 filed Dec. 7, 1984 and now abandoned which is a continuation-in-part of application Ser. No. 491,114, filed May 3, 1983 (now abandoned), which in turn is a continuation-in-part of Application, Ser. No. 309,852 filed Oct. 8, 1981 now abandoned.

BACKGROUND OF THE INVENTION

This invention is concerned with novel ocular inserts, with or without a pharmacologically active agent, comprising low molecular weight polymers including polyvinyl alcohol which do not cause blurred vision to the same extent as hydroxy propylcellulose of high molecular weight and which when formulated with enteric coating materials as a constituent of the matrix provides a means for controlling and predicting dissolution rates for slow release and prolonged residence times.

Solid ocular inserts are now well known in the art and they are generally a great advance over the prior liquid and ointment forms of medication. However, the prior art solid biosoluble ocular inserts frequently caused blurred vision because the high molecular weight polymers commonly employed altered the viscosity and refractive index of the tear film. These changes resulted in the formation of "Schlieren" or discontinuities in the precorneal tear film. The prior art solid biosoluble inserts also served to augment the blurring by the presence of a large volume of the gelatinized, hydrated polymers which tended to fracture into fragments due to blinking, giving rise to a potentially more rapid dissolution.

Now with the present invention there is provided ocular inserts that minimize the blurred vision effect by providing materials that do not materially change the viscosity and index of refraction of the tear film and optionally provide those materials at a rate sufficiently slowly as to provide only low volumes of the solubilized polymers. In addition, the compositions described do not form gelatinous masses in the cul-de-sac.

DESCRIPTION OF THE INVENTION

The novel low-vision-blurring matrices of the ocular inserts of this invention comprise a number of different components in various relative amounts. The inserts produced therefrom may or may not include a pharmacologically active agent. The components of the matrices are:

Polyvinyl Alcohol: This component is one of the principal matrix materials giving the insert its desired shape and integrity. The particular polyvinyl alcohol useful in the novel matrix has a molecular weight between about 2000 and 4000 and forms about 10% to about 100% by weight of the finished product.

Plasticizer: The matrices of the ocular inserts prepared in accordance with this invention may also contain plasticizers to make the ophthalmic inserts more pliable and to aid processing. Plasticizers suitable for this purpose must, of course, also be completely soluble in the lacrimal fluids of the eye. Examples of suitable plasticizers are water, polyethylene glycol, propylene glycol, glycerin, trimethylol propane, di- and tripropylene glycol, hydroxypropylsucrose and the like. Typically, such plasticizers can be present in the ophthalmic insert in an amount ranging from about 0% to about 20% by weight. A particularly preferred plasticizer is glycerin which is present in amounts of at least about 1.0% up to about 10%.

Hydroxypropyl cellulose: The hydroxypropyl cellulose useful in the formulation of this invention is of low molecular weight from about 30,000 to about 100,000. It is an optional component and is present in amounts from 0–30% by weight of the finished insert.

Polyvinylpyrrolidone: Polyvinylpyrrolidone is an optional component present in amounts from 0 to about 30% by weight and its presence or absence is dictated by the nature of the pharmacologically active agent that may be included. It complexes with certain materials such as indomethacin and is known to bind with certain tissue and thus has the potential of creating a depot type of medication.

Monosaccharide alcohol: Mannitol, sorbitol, or any of the other sugar alcohols, but especially mannitol, optionally may be included as a component of the insert as a diluent up to about 30% by weight of the total.

Enteric Coating Polymer: An optional component is one of the several known enteric coating polymers such as hydroxypropylmethylcellulose phthalate, cellulose acetate phthalate, hydroxypropylmethyl cellulose acid succinate, or acrylic acid polymer, which is not present as a coating, but rather as a component of the matrix, being homogeneously distributed therein. It constitutes up to about 75% by weight of the total and serves to provide a slow even release of pharmacologically active agent or a slow-release source of the polymer itself or the other components such as polyvinyl alcohol and hydroxypropylmethylcellulose. Incorporation of one of the enteric coating materials extends the dissolution rate from about 15 minutes up to about 24 hours, depending on the relative amount of the material.

Phrmacologically active Agent: If the novel ocular insert of this invention is intended for delivery of a pharmacologically active agent it is incorporated therein in an amount up to about 25% by weight and for the more active agents, amounts up to about 5% by weight are adequate. The matrix, comprising the other components, is adjusted appropriately so that the matrix constitutes about 75–99% by weight of the ocular insert. Suitable drugs for use in therapy with the ocular drug delivery system of the invention include, without limitation, drugs that produce a physiologically or pharmacologically localized or systemic effect in animals, including warm blooded mammals, human and primates, valuable domestic household, sport or farm animals such as horses, dogs, cats, cattle, sheep and the like; or for administering to laboratory animals such as mice, monkeys, rats, rabbits and guinea pigs. The active drugs that can be administered by the novel drug delivery system of the invention include, without limitation: antibiotics such as tetracycline, chlortetracycline, bacitracin, neomycin, polymyxin, norfloxacin, gramicidin, oxytetracycline, chloramphenicol, gentamycin, and erythromycin; antibacterials such as sulfonamides, sulfacetamide, sulfamethizole and sulfisoxazole; antivirals, including idoxuridine, acyclovir and related structures such as 9-(1,3-dihydroxy-2-propoxymethyl)guanine; and other antibacterial agents such as nitrofurazone and sodium propionate; anti-allergenics such as antazoline, methapyriline, chlorpheniramine, pyrilamine and prophenpyridamine; steroidal anti-inflammatories such as hydrocortisone, hydrocortisone acetate, dexamethasone, dexamethasone 21-phosphate, fluocinolone, medrysone, prednisolone, methylprednisolone, prednisolone 21-phosphate, prednisonolone acetate, fluoromethalone, betamethasone and triamcinolone; non-steroidal anti-inflammatories such as indomethacin, sulindac and aspirin; decongestants such as phenylephrine, naphazoline, and tetrahydrazoline; miotics and anticholinesterases such as pilocarpine, eserine, carbachol, di-isopropyl fluorophosphate, phospholine iodide, and demecarium bromide; mydriatics such as atropine sulfate, cyclopentolate, homatropine, scopolamine, tropicamide, eucatropine, and hydroxyamphetamine; sympathomimetics such as epinephrine; $\beta$-blockers such as propanolol or timolol maleate; topically effective carbonic anhydrase inhibitors such as 6-hydroxy-2-sulfamoylbenzo[b]thiophene, 6-acetoxy-2-sulfamoylbenzo[b]thiophene, or 5,6-dihydro-4H-4-hydroxythieno[2,3-b]thiopyran-2-sulfonamide-7,7-dioxide.

Drugs contained in the insert can be in different forms, such as uncharged molecules, components of molecular complexes or non-irritating, pharmacologically acceptable derivatives thereof. Simple derivatives of the drugs such as pharmaceutically acceptable ethers, esters, amides, and the like which have desirable retention and release characteristics but which are easily hydrolyzed by body pH, or enzymes to active forms, and the like, can be employed.

The amount of drug incorporated in the system varies depending on the drug, the desired therapeutic effect, and the time span for which the system provides therapy. Since a variety of systems in a variety of sizes and shapes are intended to provide dosage regimens for therapy for a variety of maladies, there is no critical upper limit on the amount of drug incorporated in the system. The lower limit too will depend on the activity of the drug and the time span of its release from the system. Thus, it is not practical to define a range for the therapeutically effective amount of drug to be incorporated in or released by the system. However, the amount of drug present is generally nonlimited and it is an amount equal to or larger than the amount of drug that on its release from the system is effective for bringing about the drug's effects. Generally, an ocular system containing a pharmacologically active agent will contain from 1 microgram to about 700 micrograms of drug or more, for releasing the drug to the eye at art recognized dosage rates.

The compositions of this invention can be prepared by various methods. Thus, the drug and the polymer(s) can be dissolved in a suitable solvent and the solution evaporated to afford a thin film comprising the polymer(s) and the drug which can then be subdivided to prepare suitable inserts containing the desired amount of the medicament. Alternatively, and in accordance with a preferred embodiment of our invention, we find that the inserts can be prepared most conveniently using the thermoplastic properties of the polymer(s) described above. For example, the medicament and the polymer(s) can be warmed together at temperatures between about 150° F. and 400° F. and the resulting mixture compression molded to form a thin film. It is generally preferred to prepare the inserts by compression molding or extrusion in accordance with procedures which are well known in the art. The compression molded or extruded product can then be subdivided to afford inserts of suitable size for administration in the eye. For example, castings or compression molded films having a thickness of about 0.5 mm. to 1.5 mm. can be subdivided to obtain suitable inserts in the form of squares, rectangles, circles, semi-circles, and the like containing the desired amount of active ingredient. Rectangular segments of the cast or compressed film having a thickness between about 0.5 and 1.5 mm. can be cut to afford shapes such as rectangular plates of 4×5-15 mm. or ovals of comparable size. Similarly, extruded rods having a diameter between about 0.5 and 1.5 mm. can be cut into suitable sections to provide the desired dosage of medicament. For example, rods of 1.0 to 1.5 mm. in diameter and up to 5 mm. long are found to be satisfactory. The inserts may also be directly formed by injection molding. All of the ophthalmic inserts prepared in accordance with the present invention should be formed so that they do not have any sharp edges or corners which could cause damage to the eye.

EXAMPLE 1

The following table exemplifies 6 typical formulations with their respective dissolution times.

TABLE I

| Composition | Composition of 6 Ophthalmic Insert Matrices |  |  |  |  |  |
|---|---|---|---|---|---|---|
|  | Mg. per 3 mg. Insert |  |  |  |  |  |
|  | A | B | C | D | E | F |
| Polyvinyl Alcohol | 1.50 | 0.45 | 1.50 | 2.10 | 1.50 | 3.0 |
| Hydroxypropyl cellulose EF | 0.60 | — | — | — | — | — |
| Hydroxypropyl methylcellulose phthalate | — | 2.25 | — | — | 1.35 | — |
| Polyvinylpyrrolidone | — | — | 0.60 | — | — | — |
| Mannitol | 0.75 | — | 0.75 | 0.75 | — | — |
| Glycerin | 0.15 | 0.30 | 0.15 | 0.15 | 0.15 | — |
| Timolol maleate | — | — | — | — | — | — |
| Estimated dissolution time in vivo based on in vitro and in vivo data in rabbits | 15 min. | 6–7 hrs. | 15 min. | 15 min. | 1–2 hrs. | 30 min |

Formulation A is prepared as follows:

Glycerin and mannitol are blended together to form a granular mass. Polyvinyl alcohol 40/10 (mn 2000) is gradually added until a uniform mixture is obtained. Finally, the hydroxypropyl cellulose is added and the entire mixture extruded using a twin screw extruder to form a strand 1 mm in diameter which can be cut into lengths of the desired size.

The other formulations are prepared in substantially the same manner.

EXAMPLE 2

Assay of Vision Blurring Potential

An in vivo assessment of the blurred vision potential is made using dogs. An insert is placed into the cul-de-sac of a conditioned female beagle dog. Observations of the keratoscopic mires using a self illuminated placido disk (Klein Keratoscope) are then made at regular intervals until the insert is completely dissolved. The degree of distortion of the mires is graded on a scale of one to six. A plot of degree of distortion versus time is made and the area under the curve measured. This value is termed the distortion index. A second value obtained from the measurement is the duration of distortion which is defined as the total time that distortion occurs during a given experiment. For purposes of accuracy, each insert composition is tested in 3 animals.

RESULTS

TABLE II

| Insert | Distortion Index | Duration of Distortion |
|---|---|---|
| 5 mg Hydroxypropyl cellulose HF | 415 | >120 min. |
| 5 mg Hydroxypropyl cellulose JF | 330 | >120 min. |
| 5 mg Polyvinyl alcohol 30-20* | 120 | 120 min. |
| 2.5 mg Hydroxypropyl cellulose EF | 297 | 180 min. |
| Matrix A of Example 1 | 5 | 10 min. |
| B of Example 1 | 0 | 0 min. |
| C of Example 1 | 0 | 0 min. |
| D of Example 1 | 8 | 10 min. |
| E of Example 1 | 2 | 5 min. |
| F of Example 1 | 18 | 15 min. |

*m.w.~20,000

EXAMPLE 3

Evaluation of Inserts in Human Volunteers

Non-medicated inserts of compositions A–F of Example 1 were evaluated for their relative abilities to cause blurred vision in humans with the following results:

TABLE III

| Insert | % Subjects experiencing blurred vision |
|---|---|
| A | 67% |
| B | 36% |
| C | 67% |
| D | 36% |
| E | 75% |
| Lacrisert ® | 64% |

The tests were conducted in a double-blind protocol involving 11–14 patients.

EXAMPLE 4

Medicated Inserts

The inserts of compositions B and D of Example 1 showing the least vision-blurring potential (Example 3) were prepared including 25 mcg. of timolol. These inserts were used along with non-medicated inserts (placebos) to investigate their effect on intraocular pressure over a period of time in 32 human patients in a double-masked, completely randomized cross-over study.

Intraocular pressure was measured at baseline and 2, 4, 7, and 24 hours following administration of each insert. Placebo inserts were compared at all five time periods and neither were significantly different from the other. Loaded inserts (B and D) were compared at all time points. The baseline reading for the slower dissolving Insert B with timolol was significantly higher from the average baseline reading for Insert D (loaded, $P<0.05$). At the 2 hour reading, values for the B-timolol-loaded inserts were again significantly higher ($P<0.001$). No other differences were noted. The slow dissolving insert (B) reduced intraocular pressure significantly at the 4, 7, and 24-hour readings when compared to placebo. The faster dissolving Insert D (usually dissolves within 2 hours) significantly reduced IOP at all time points when compared to placebo (see Table IV).

TABLE IV

| | 0 Hour | t | 2 Hours | t | 4 Hours | t | 7 Hours | t | 24 Hours | t |
|---|---|---|---|---|---|---|---|---|---|---|
| Insert B* | | | | | | | | | | |
| Placebo | 15.1 ± 3.1 | | 14.0 ± 3.0 | | 13.8 ± 2.8 | | 14.0 ± 3.2 | | 14.6 ± 3.3 | |
| Timolol | 16.0 ± 3.6 | −1.62 | 13.3 ± 3.5 | 1.250 | 11.7 ± 3.6 | 4.316* | 12.4 ± 2.8 | 3.324* | 13.3 ± 2.8 | 2.946* |
| N = | 32 | | 32 | | 32 | | 31 | | 31 | |
| P = | | NS | | NS | | 0.0001 | | 0.005 | | 0.010 |
| Insert D* | | | | | | | | | | |
| Placebo | 15.0 ± 3.7 | | 14.9 ± 4.0 | | 14.1 ± 3.4 | | 14.3 ± 3.1 | | 15.6 ± 3.4 | |
| Timolol | 14.8 ± 3.7 | 0.399 | 11.1 ± 3.7 | 7.741* | 11.0 ± 3.0 | 7.306* | 11.8 ± 2.6 | 6.187 | 13.3 ± 3.0 | 4.678* |
| N = | 31 | | 31 | | 32 | | 32 | | 30 | |
| P = | | NS | | 0.001 | | 0.001 | | 0.001 | | 0.001 |

The mean was calculated for each pair of IOP's for each allocation at each reading.
These values were compared for the above.
*Insert dissolved up to 24 hrs +
**Insert dissolved within 2 hrs for most subjects
(P is based on df = 30)

It is to be noted that the amount of timolol maleate per insert is approximately 25% less than would be found in a drop of Timoptic 0.1% ®, a commercially available formulation, and yet the effect of the novel medicated inserts on intraocular pressure is considerably longer lasting than the times experienced with the commercial liquid preparation.

EXAMPLE 5

Medicated Inserts

Treatment of Herpes Simplex Keratitis with 9-(1,3-dihydroxy-2-propoxymethyl)guanine (L-645,383) in Drops and Ophthalmic Inserts This experiment was conducted to determine the effectiveness of L-645,383 when administered in drops and ophthalmic insert, on rabbits infected with McKrae strain HSV1 virus. There were 6 groups of 4 animals each treated as follows:

| Treatment Group | Treatments per Day | Medication |
| --- | --- | --- |
| 1 | 2 | L-645,383 drop, 50 mcg/drop |
| 2 | 2 | L-645,383 drop, 150 mcg/drop |
| 3 | 2 | L-645,383 drop, 300 mcg/drop |
| 4 | 2 | Placebo drop |
| 5 | 1 | L-645,383 insert, 300 mcg/insert |
| 6 | 1 | L-645,383 insert, 600 mcg/insert |

Ophthalmic evaluations were conducted daily on each eye of each animal using a slit-lamp biomicroscope.

Conclusions

1. Animals receiving 50, 150, or 300 mcg of L-645,383 in drops, 2×/day, or 300 or 600 mcg of L-645,383 in ophthalmic insert, 1×/day, showed enhanced protection over placebo treated animals as measured by average corneal epithelium scores.

2. Animals receiving 50, 150, or 300 mcg of L-645,383 in drops, 2×/day, or 300 or 600 mcg of L-645,383 in ophthalmic insert, 1×/day, showed enhanced protection over placebo treated animals as measured by average stroma scores.

3. Animals receiving 50 mcg of L-645,383 in drops, 2×/day, showed enhanced protection over placebo treated animals as measured by average conjunctiva scores.

EXAMPLE 6

Indomethacin Ophthalmic Inserts

The inserts of compositions B and D of Example 1 showing the least vision-blurring potential (Example 3) were prepared to include 800 g of indomethacin each. A 1% (w/w) indomethacin aqueous suspension was also prepared. Rabbit eyes were treated with the inserts and the aqueous suspension (500 g) and the tear fluids were assayed at various times. Quantifiable levels of indomethacin were found at one minute after administration of the suspension, but at no other time up to two hours. Indomethacin could be quantitated in tear fluid up to one hour after administration of insert D and trace levels were seen up to five hours post administration. Tear fluid samples obtained up to 24 hours after administration of the hydroxypropyl methylcellulose phthalate inserts (B) were largely negative for indomethacin. Only one animal exhibited detectable levels of indomethacin (at one and eight hours).

EXAMPLE 7

Norfloxacin (MK-366) Ophthalmic Inserts

In order to obtain some starting values and also in order to test the methods, a probe study was conducted. Fifty mcl of a 2% non-buffered isotonic solution of MK-366 at pH 5.3 was instilled with an Eppendorf pipet in the right eye of 6 albino rabbits. Tears were collected at T=30, 60, 120, 180, 300, and 360 minutes, their pH was then measured with pH paper. The MK-366 levels obtained are given in Table I.

TABLE I

Concentration of MK-366 in Tear Fluid and Aqueous Humor After Instillation of 50 mcl of a 2% Solution

| Sampling Time T | Number of eye | Tear Concentration in mcg/ml ± s.e.m. |
| --- | --- | --- |
| 30 | 6 | 2650 ± 600 |
| 60 | 6 | 900 ± 250 |
| 120 | 6 | 530 ± 100 |
| 180 | 6 | 550 ± 180 |
| 300 | 5 | 240 ± 56 |
| 360 | 5 | 370 ± 100 |

Inserts of MK-366 in the fast dissolving matrix: Mannitol 25%, Glycerin 5%, Polyvinyl alcohol (Gelvatol 40-10) 70% were dissolved in water. MK-366 was added to form a suspension. The film was cast from a suspension of MK-366 in the matrix solution, and also from a solution of MK-366 in the matrix obtained after addition of a quantitative amount of HCl to form the hydrochloride. The content uniformity determined by U.V. on 10 inserts of each category was:

MK-366 inserts: 393 mcg of MK-366±R.S.D. 3.6% per insert of 3.4 mg (average weight)

MK-366 HCl inserts: 457 mcg of MK-366±R.S.D. 3.2% per insert of 5.3 mg (average weight)

The in-vitro dissolution rate of each type of insert was determined in the USP apparatus I using 100 RPM and 150 ml round bottom flasks containing 120 ml of water at 37° C. The percent of MK-366 dissolved was respectively 44, 65, 83, and 86% after 15, 30, 60 and 240 minutes for the MK-366 inserts. The MK-366 was completely dissolved (96%) after 5 minutes in the MK-366 HCl inserts.

The inserts were then sterilized by gamma irradiation between 1.4 and 1.8 Mrads. The irradiated samples were assayed by HPLC; the assay values obtained were 389 mcg/insert±R.S.D. 4.7% (n=5) for the MK-366 inserts and 446 mcg/insert±R.S.D. 1.6% (n=5) for the MK-366 HCl inserts.

The irradiated inserts were well tolerated in a 3 day rabbit eye irritation study. The tear fluid level of MK-366 was determined at 2, 4, 8, and 18 hours after treatment of rabbits in both eyes with inserts. The rabbits were kept in restraint boxes during the entire test.

The results obtained given in Table II show that levels much above the minimum targetted concentration (10 mcg/ml) are maintained for at least 18 hours. After 8 hours, inserts were not completely dissolved in 3 out of 6 eyes for the MK-366 inserts, and only in 1 out of 6 eyes for the MK-366 HCl inserts. All inserts were dissolved after 18 hours.

TABLE II

Concentration of MK-366 in Rabbit Tear Fluid After Treatment with MK-366 Inserts

| Insert Type | Sampling Time in Hrs | Tear Concentration mcg/ml ± s.e.m. | Number of eyes |
| --- | --- | --- | --- |
|  | 2 | 245 ± 18 | 6 |
| MK-366 | 4 | 390 + 115 | 6 |
| (389 mg/ | 8 | 210 + 45 | 6 |
| insert) | 18 | 85 + 53 | 6 |
| MK-366 HCl | 2 | 330 + 160 | 6 |
| (446 mg of | 4 | 265 + 66 | 6 |
| MK-366/ | 8 | 85 + 20 | 6 |
| insert) | 18 | 75 + 29 | 5 |

What is claimed is:

1. A non-vision blurring ocular insert comprising 75–100% of a matrix comprising, in percentage parts by weight:
   (i) 15% polyvinyl alcohol (m.w. 2000–3000);
   (ii) 10% glycerin; and
   (iii) 75% hydroxypropylmethylcellulose phthalate, and 0–25% of a pharmacologically active agent.

2. A non-vision bluring ocular insert comprising 75–100% of a matrix comprising, in percentage parts by weight:
   (i) 70% polyvinyl alcohol (m.w. 2000–3000);
   (ii) 5% glycerin; and
   (iii) 25% mannitol; and 0–25% of a pharmacologically active agent.

* * * * *